US012575759B2

(12) United States Patent　　　(10) Patent No.:　US 12,575,759 B2

Tsukahara　　　(45) Date of Patent:　Mar. 17, 2026

(54) MEDICAL IMAGE DIAGNOSTIC APPARATUS, COUCH DEVICE, AND CONTROL METHOD

(71) Applicant: CANON MEDICAL SYSTEMS CORPORATION, Otawara (JP)

(72) Inventor: Yutaro Tsukahara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 149 days.

(21) Appl. No.: 18/535,448

(22) Filed: Dec. 11, 2023

(65) Prior Publication Data

US 2024/0188849 A1　　Jun. 13, 2024

(30) Foreign Application Priority Data

Dec. 12, 2022　(JP) ................................. 2022-197885
Nov. 24, 2023　(JP) ................................. 2023-199041

(51) Int. Cl.
| | |
|---|---|
| *A61B 5/107* | (2006.01) |
| *A61B 5/00* | (2006.01) |
| *A61B 6/04* | (2006.01) |
| *A61G 7/10* | (2006.01) |

(52) U.S. Cl.
CPC ............ *A61B 5/1079* (2013.01); *A61B 5/704* (2013.01); *A61B 5/7267* (2013.01); *A61B 6/04* (2013.01); *A61G 7/1019* (2013.01)

(58) Field of Classification Search
CPC ..... A61B 5/1079; A61B 5/704; A61B 5/7267; A61B 6/04; A61B 6/032; A61B 6/0407; A61G 7/1019; G01G 19/445
See application file for complete search history.

(56) References Cited

U.S. PATENT DOCUMENTS

| | | | |
|---|---|---|---|
| 9,592,023 B2 | 3/2017 | Tanaka et al. | |
| 2019/0183382 A1* | 6/2019 | Akatsu | A61B 5/6892 |
| 2022/0346710 A1* | 11/2022 | Fuchibe | A61B 5/1072 |

FOREIGN PATENT DOCUMENTS

| | | | |
|---|---|---|---|
| DE | 10 2009 043 532 A1 | 9/2010 | |
| DE | 10 2011 080 691 A1 | 2/2013 | |
| JP | 2010017457 A | * | 1/2010 |
| JP | 5 329141 B2 | 10/2013 | |
| WO | WO 2014/084291 | 6/2014 | |

OTHER PUBLICATIONS

Extended European Search Report dated Apr. 16, 2024 in corresponding European Patent Application No. 23215637.2, 7 pages.

* cited by examiner

*Primary Examiner* — Kaitlyn E Sebastian

(74) *Attorney, Agent, or Firm* — Oblon, McClelland, Maier & Neustadt, L.L.P.

(57)　　　ABSTRACT

A medical image diagnostic apparatus according to an embodiment includes a table-top, a measurement unit, and processing circuitry. The table-top places thereon a subject. The measurement unit outputs a measurement signal corresponding to weight of the subject placed on the table-top. The processing circuitry estimates the weight of the subject placed on the table-top, based on the measurement signal and arrangement information on arrangement of the measurement unit.

11 Claims, 8 Drawing Sheets

FIG. 1

MEDICAL IMAGE DIAGNOSTIC APPARATUS, COUCH DEVICE, AND CONTROL METHOD

CROSS-REFERENCE TO RELATED APPLICATIONS

This application is based upon and claims the benefit of priority from Japanese Patent Application No. 2022-197885, filed on Dec. 12, 2022 and Japanese Patent Application No. 2023-199041, filed on Nov. 24, 2023, the entire contents of which are incorporated herein by reference.

FIELD

Embodiments described herein relate generally to a medical image diagnostic apparatus, a table, and a control method.

BACKGROUND

Conventionally, a table of an X-ray Computed Tomography (CT) apparatus has a weight measurement mechanism for measuring the weight of a subject placed on a table.

However, depending on the mode of measurement such as the posture and position of a subject on the table, a moment load applied to a load cell that measures the weight of the subject differs. Then, errors caused by the moment load or the like reduce the measurement accuracy.

BRIEF DESCRIPTION OF THE DRAWINGS

FIG. 1 is a diagram illustrating an example of a configuration of an X-ray CT apparatus according to a first embodiment;

DETAILED DESCRIPTION

Figure 2:
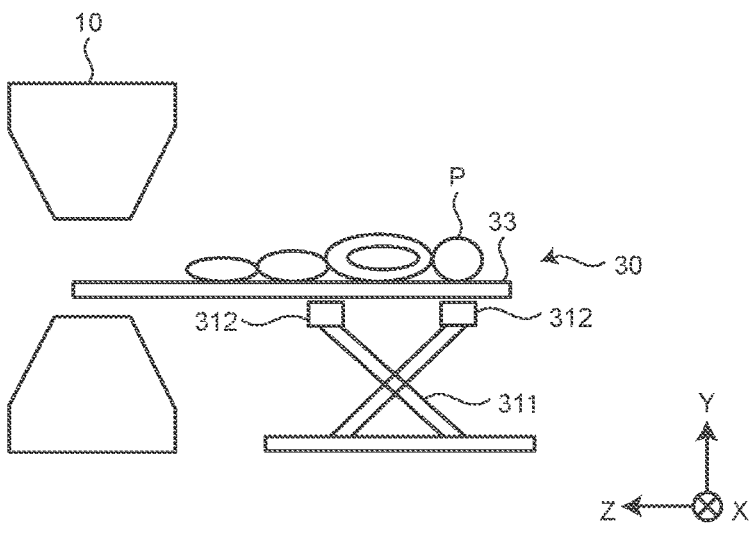
FIG. 2 is a diagram illustrating an example of a schematic configuration of the inside of a table according to the first embodiment.

A medical image diagnostic apparatus according to an embodiment includes a table-top, a measurement unit, and processing circuitry. The table-top places thereon a subject. The measurement unit outputs a measurement signal corresponding to weight of the subject placed on the table-top. The processing circuitry estimates the weight of the subject placed on the table-top, on the basis of the measurement signal and arrangement information on arrangement of the measurement unit.

Hereinafter, a medical image diagnostic apparatus, a table, and a control method according to embodiments will be described in detail with reference to the accompanying drawings. In the following embodiments, the parts with the same reference numerals perform the same operation, and duplicate description will be omitted as appropriate.

First Embodiment

Figure 1:
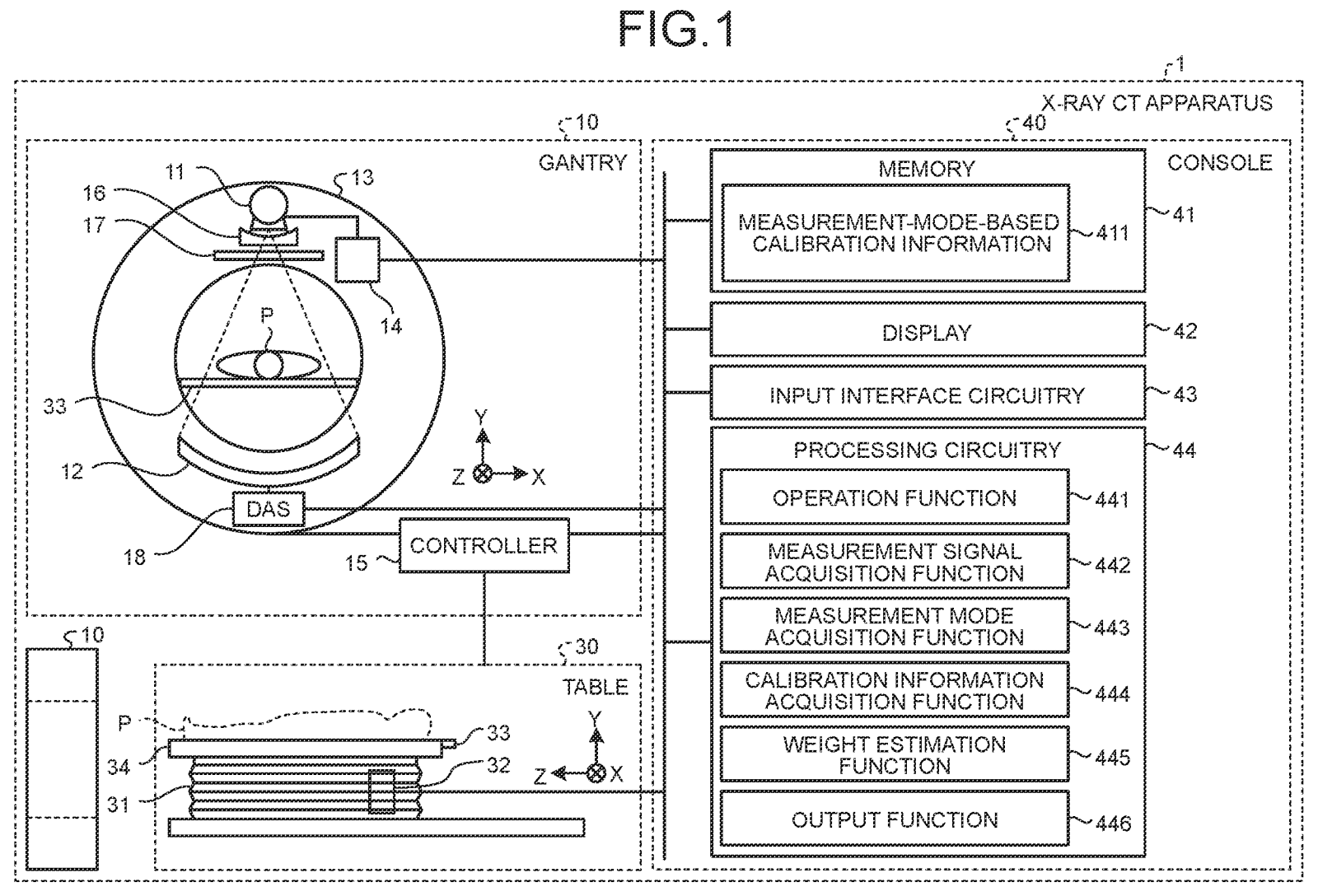

FIG. 1 is a diagram illustrating an example of a configuration of an X-ray CT apparatus 1 according to a first embodiment. As illustrated in FIG. 1, the X-ray CT apparatus 1 includes a gantry 10, a table 30, and a console 40. The X-ray CT apparatus 1 is an example of a medical image diagnostic apparatus.

In FIG. 1, the Z-axis direction is the longitudinal direction of the rotation axis of a rotation frame 13 or a table-top 33 of the table 30 in a non-tilted state. Moreover, the X-axis direction is the axial direction orthogonal to the Z-axis direction, and that is horizontal to the floor surface. Furthermore, the Y-axis direction is the axial direction orthogonal to the Z-axis direction and the X-axis direction, and that is perpendicular to the floor surface. FIG. 1 is an illustration of the gantry 10 from multiple directions for the purpose of explanation, and the X-ray CT apparatus 1 includes a single gantry 10.

The gantry 10 includes an X-ray tube 11, an X-ray detector 12, the rotation frame 13, X-ray high-voltage circuitry 14, a controller 15, a wedge 16, a collimator 17, and a Data Acquisition System (DAS) 18. The gantry 10 is also referred to as a mounting device.

The X-ray tube 11 is a vacuum tube including a cathode (filament) that generates thermal electrons, and an anode (target) that receives collision of thermal electrons to generate X-rays. When high voltage is applied from the X-ray high-voltage circuitry 14, the X-ray tube 11 generates X-rays to be applied to the subject P, by emitting thermal electrons from the cathode toward the anode. For example, the X-ray tube 11 includes a rotating anode X-ray tube that generates X-rays by irradiating a rotating anode with thermal electrons.

The X-ray detector 12 detects X-rays emitted from the X-ray tube 11 and that have passed through the subject P, and outputs a signal corresponding to the detected X-ray dose to the DAS 18. For example, the X-ray detector 12 includes a plurality of detection element arrays in which a plurality of detection elements are arranged in a channel direction (channel direction) along a single arc centered on the focal point of the X-ray tube 11. For example, the X-ray detector 12 has a structure in which the detection element arrays in which the detection elements are arranged in the channel direction are arranged in a column direction (slice direction, row direction).

For example, the X-ray detector 12 is an indirect conversion detector including a grid, a scintillator array, and an optical sensor array. The scintillator array includes a plurality of scintillators. The scintillator has a scintillator crystal that outputs light with a photon quantity corresponding to the incident X-ray dose. The grid has an X-ray shielding plate that is disposed on the surface of the scintillator array on the X-ray incidence side, and that absorbs scattered X-rays. The grid may also be referred to as a collimator (one-dimensional collimator or two-dimensional collimator). The optical sensor array has a function of converting the light from the scintillator into an electric signal corresponding to the amount of light. For example, the optical sensor array includes an optical sensor such as a photodiode. The X-ray detector 12 may also be a direct conversion type detector including a semiconductor element that converts the incident X-rays into electrical signals.

The rotation frame 13 is an annular frame that supports the X-ray tube 11 and the X-ray detector 12 such that the X-ray tube 11 and the X-ray detector 12 face each other, and that rotates the X-ray tube 11 and the X-ray detector 12 by the controller 15. For example, the rotation frame 13 is a casting made of aluminum. In addition to the X-ray tube 11 and the X-ray detector 12, the rotation frame 13 can further support the X-ray high-voltage circuitry 14, the wedge 16, the collimator 17, the DAS 18, and the like. Furthermore, the rotation frame 13 can further support various components not illustrated in FIG. 1. The various components supported by the rotation frame 13 will be described below. The rotation frame 13 is also referred to as a rotation base, a rotation body, or the like. Moreover, in the gantry 10, the rotation frame 13 and a portion that rotates and moves with the rotation frame 13 may also be referred to as a rotation part.

The X-ray high-voltage circuitry 14 includes high-voltage generation circuitry that includes an electric circuit such as a transformer (transformer) and a rectifier and that generates a high voltage to be applied to the X-ray tube 11, and an X-ray controller that controls the output voltage according to the X-rays generated by the X-ray tube 11. The high-voltage generation circuitry may be a transformer type or an inverter type. The X-ray high-voltage circuitry 14 may be installed on the rotation frame 13 or may be installed on a fixing frame, which is not illustrated.

The controller 15 includes processing circuitry including a Central Processing Unit (CPU) or the like, and a drive mechanism such as a motor and an actuator. Upon receiving an input signal from input interface circuitry 43, which will be described below, the controller 15 controls the operation of the gantry 10 and the table 30. For example, the controller 15 controls the rotation of the rotation frame 13, the tilt of the gantry 10, the operation of the table 30 and the table-top 33, and the like. As an example, as a control to tilt the gantry 10, the controller 15 rotates the rotation frame 13 around an axis parallel to the X-axis direction, according to the input inclination angle (tilt angle) information. The controller 15 may be provided on the gantry 10 or may be provided on the console 40.

The wedge 16 is a filter for adjusting the dose of X-rays emitted from the X-ray tube 11. Specifically, the wedge 16 is a filter that attenuates the X-rays emitted from the X-ray tube 11 by allowing the X-rays to pass therethrough such that the X-rays emitted from the X-ray tube 11 to the subject P have a predetermined distribution. For example, the wedge 16 is a wedge filter or a bow-tie filter, and is a filter obtained by processing aluminum or the like to have a predetermined target angle and a predetermined thickness.

The collimator 17 is a lead plate or the like to narrow the irradiation range of the X-rays that have passed through the wedge 16. The collimator 17 forms a slit by combining a plurality of lead plates or the like. The collimator 17 may also be referred to as an X-ray diaphragm. Moreover, in FIG. 1, the wedge 16 is disposed between the X-ray tube 11 and the collimator 17. However, the collimator 17 may be disposed between the X-ray tube 11 and the wedge 16. In this case, the wedge 16 attenuates the X-rays emitted from the X-ray tube 11 and the irradiation range of which is limited by the collimator 17 by allowing the X-rays to pass therethrough.

The DAS 18 collects signals of the X-rays detected by the detection elements of the X-ray detector 12. For example, the DAS 18 includes an amplifier that performs an amplification process on an electrical signal output from each detection element, and an A/D converter that converts the electrical signal into a digital signal. The DAS 18 generates detection data.

The detection data generated by the DAS 18 is transmitted from a transmitter provided on the rotation frame 13 and that includes a Light Emitting Diode (LED), to a receiver provided on a non-rotating portion (for example, a fixing frame or the like. Not illustrated in FIG. 1) of the gantry 10 and that includes a photodiode, by optical communication, and is transferred to the console 40. For example, in this example, the non-rotating portion is a fixing frame that rotatably supports the rotation frame 13 or the like. The transmission method of data from the rotation frame 13 to the non-rotating portion of the gantry 10 is not limited to optical communication, but any non-contact data transmission method or a contact data transmission method may be used.

The table 30 is an apparatus for placing and moving the subject P to be photographed, and includes a base 31, table drive circuitry 32, the table-top 33, and a support frame 34. The base 31 is a housing that movably supports the support frame 34 in the vertical direction. The table drive circuitry 32 is a drive mechanism that moves the table-top 33 on which the subject P is placed in the long axis direction of the table-top 33, and includes a motor, an actuator, and the like. The table-top 33 provided on the top surface of the support frame 34 is a plate on which the subject P is placed. In addition to the table-top 33, the table drive circuitry 32 may also move the support frame 34 in the long axis direction of the table-top 33.

FIG. 2 is a diagram illustrating an example of a schematic configuration of the inside of the table 30 according to the first embodiment. The table 30 includes an X-shaped link 311 that supports, lifts, and lowers the table-top 33 inside the base 31. For example, the X-shaped link 311 lifts and lowers the table-top 33 by adjusting the width thereof in the Z-axis direction using a joint provided substantially at the center where the two links are overlapped in an X-shape as a rotation axis. Moreover, two X-shaped links 311 are arranged side by side in the X-axis direction.

Moreover, in the base 31, a weight sensor 312 is disposed between the X-shaped link 311 and the table-top 33. Two X-shaped links 311 are arranged side by side in the X-axis direction. That is, the base 31 includes a total of four weight sensors 312 between the link and the table-top 33. In addition to the four weight sensors 312, the base 31 may also include five or more weight sensors 312, or three or less weight sensors 312.

The weight sensor 312 outputs a measurement signal corresponding to the weight of an object such as the subject P placed on the table-top 33. The weight sensor 312 is an example of a measurement unit. The weight sensor 312 is implemented by a sensor for measuring weight such as a load cell and a piezoelectric element. The weight sensor 312 is a sensor disposed between the table-top 33 and the X-shaped link 311 for movably supporting the table-top 33, and that measures the weight of an object placed on the table-top 33. The X-shaped link 311 is an example of a support unit. For example, when an object is placed on the weight sensor 312, the resistance value changes according to the distortion caused by the weight of the object. The weight sensor 312 outputs a measurement signal indicating the measurement value based on the resistance value. That is, the weight sensor 312 outputs a measurement signal indicating the weight of the subject P placed on the table-top 33.

The console 40 includes a memory 41, a display 42, an input interface circuitry 43, and processing circuitry 44. The console 40 is described separately from the gantry 10. However, the gantry 10 may include the console 40 or a part of the components of the console 40.

For example, the memory 41 is implemented by a semiconductor memory element such as a Random Access Memory (RAM) and a flash memory, a hard disk, an optical disc, and the like. For example, the memory 41 stores projection data and CT image data. Moreover, for example, the memory 41 stores computer programs for the circuit included in the X-ray CT apparatus 1 to implement various functions. The memory 41 may be implemented by a group of servers (cloud) connected to the X-ray CT apparatus 1 via a network.

Figure 3:
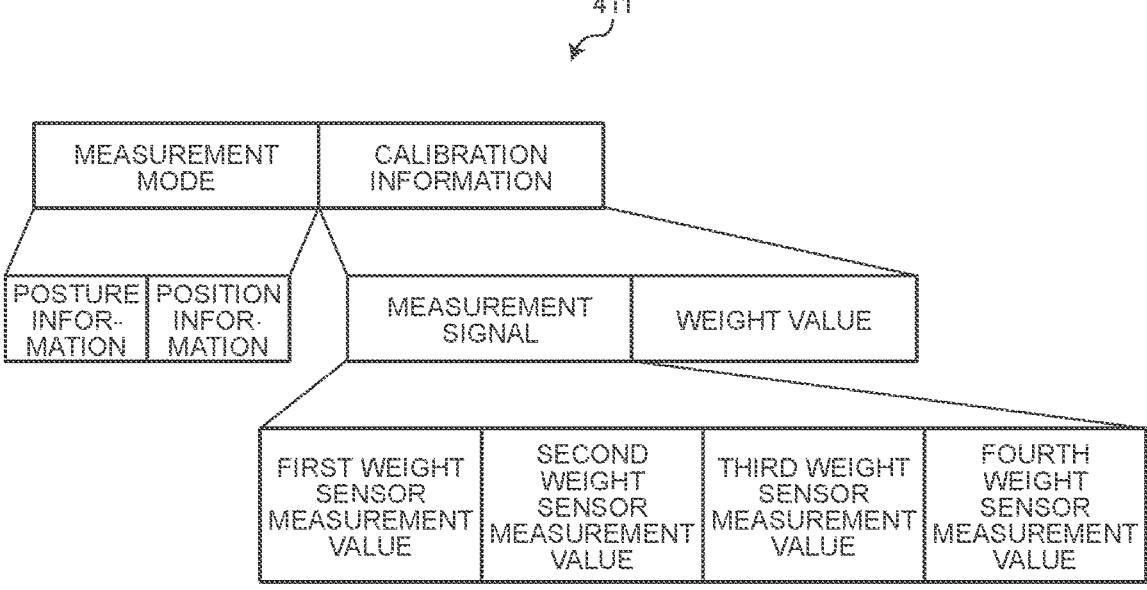
FIG. 3 is a diagram illustrating an example of a data structure of measurement-mode-based calibration information.

Moreover, the memory 41 stores measurement-mode-based calibration information 411 in which the measurement mode and the calibration information are associated with each other. The memory 41 is an example of a memory. FIG. 3 is a diagram illustrating an example of a data structure of the measurement-mode-based calibration information 411. The measurement-mode-based calibration information 411 is calibration information on each measurement mode that is a mode for measuring the weight of the subject P. The calibration information is information indicating the weight of the subject P for each measurement signal from each of the weight sensors 312.

In the table 30 in this example, different distortions occur depending on the position and posture of the subject P placed on the table-top 33. Moreover, different moment loads are applied to each of the weight sensors 312 depending on the position and posture of the subject P placed on the table-top 33. In this manner, the measurement signal of each of the weight sensors 312 differs depending on the position and posture of the subject P placed on the table-top 33.

Therefore, the X-ray CT apparatus 1 obtains calibration information corresponding to the measurement mode of the subject P, from the measurement-mode-based calibration information 411. Then, the X-ray CT apparatus 1 estimates the weight of the subject P on the basis of the acquired calibration information and the measurement signal of the weight sensor 312.

The measurement mode is information indicating the mode of weight measurement of the subject P. For example, the measurement mode includes posture information and position information. The posture information is information indicating the posture of the subject P placed on the table-top 33. For example, the posture information is information such as head-first that is the posture of the subject P inserted into the gantry 10 from the head, feet-first that is the posture of the subject P inserted into the gantry 10 from the feet, or the like. The position information is information indicating the position of the subject P placed on the table-top 33. For example, the position information is information indicating the position of the subject P in the X-axis direction, the Y-axis direction, and the Z-axis direction. For example, the position information is information indicating the position of the center of gravity of the subject P at any interval such as at every 10 millimeters on the table-top 33. Furthermore, the position information need not be provided equally such as at every 10 millimeters. Then, the measurement-mode-based calibration information 411 includes calibration information for each posture indicated by the posture information and each interval indicated by the position information. The measurement mode may also include one of the posture information and position information, in addition to both posture information and position information. Furthermore, other requirements may also be added to the measurement mode, in addition to the posture information and position information. For example, in the measurement mode, physique information indicating the physique of the subject P such as an adult or a child may also be added. Furthermore, the measurement mode may be changed as appropriate by the designer who creates the measurement-mode-based calibration information 411 or by the operation using measurement-mode-based calibration information 411. In other words, the variations of the posture indicated by the posture information and the intervals indicated by the position information may be changed as desired.

The measurement signal is a measurement value indicated by the measurement signal of each of the weight sensors 312 such as a first weight sensor measurement value, a second weight sensor measurement value, a third weight sensor measurement value, a fourth weight sensor measurement value, and the like. That is, the measurement value is the measurement results of each of the four weight sensors 312. The weight value is a value indicating the weight of the subject P placed on the table-top 33. For example, the weight value is information indicating the weight value of the subject P, when the subject P is placed on the position indicated by the position information in the posture indicated by the posture information, and when the measurement value indicated by the measurement signal is acquired. The measurement-mode-based calibration information 411 may also be stored in another storage medium, in addition to the memory 41. For example, the measurement-mode-based calibration information 411 may also be stored in a server apparatus or the like.

The display 42 displays various types of information. For example, the display 42 displays various images generated by the processing circuitry 44, and displays a Graphical User Interface (GUI) for receiving various operations from the operator. For example, the display 42 is a liquid crystal display and a Cathode Ray Tube (CRT) display. The display 42 may be a desktop type or may be configured by a tablet terminal or the like capable of performing wireless communication with the main body of the console 40. Moreover, the display 42 is an example of a display unit.

The input interface circuitry 43 converts various input operations received from the operator into electrical signals, and outputs the electrical signals to the processing circuitry 44. Moreover, for example, the input interface circuitry 43 receives input operations of scan conditions, reconstruction conditions for reconstructing CT image data, image processing conditions for generating a post-processed image from the CT image data, and the like, from the operator.

For example, the input interface circuitry 43 is implemented by a mouse, a keyboard, a trackball, a switch, a button, a joystick, a touch pad with which input operations are performed by touching an operation surface, a touch screen in which a display screen and a touch pad are integrated, a non-contact input circuit using an optical sensor, a voice input circuit, and the like. The input interface circuitry 43 may also be provided on the gantry 10. Moreover, the input interface circuitry 43 may also be configured by a tablet terminal or the like capable of performing wireless communication with the main body of the console 40. Furthermore, the input interface circuitry 43 is not limited to one having physical operation parts such as a mouse and a keyboard. For example, electrical signal processing circuitry that receives an electrical signal corresponding to an input operation from an external input device, which is provided separately from the console 40, and that outputs the electrical signal to the processing circuitry 44, is also an example of the input interface circuitry 43.

The processing circuitry 44 controls the entire operation of the X-ray CT apparatus 1. For example, the processing circuitry 44 includes an operation function 441, a measurement signal acquisition function 442, a measurement mode acquisition function 443, a calibration information acquisition function 444, a weight estimation function 445, and an output function 446. In the embodiment, each processing function performed by the operation function 441, the measurement signal acquisition function 442, the measurement mode acquisition function 443, the calibration information acquisition function 444, the weight estimation function 445, and the output function 446 is stored in the memory 41 in the form of a computer executable program. The processing circuitry 44 is a processor that reads and executes a computer program from the memory 41, and implements the function corresponding to each computer program. In other words, the processing circuitry 44 that has read out computer programs has the functions illustrated in the processing circuitry 44 in FIG. 1.

In FIG. 1, the operation function 441, the measurement signal acquisition function 442, the measurement mode acquisition function 443, the calibration information acquisition function 444, the weight estimation function 445, and the output function 446 are implemented by a single processor. However, the processing circuitry 44 can also be configured by combining a plurality of independent processors, and each processor can execute a computer program to implement the function. Moreover, in FIG. 1, a single storage circuit such as the memory 41 stores a computer program corresponding to each processing function. However, a plurality of storage circuits may be distributed and arranged, and the processing circuitry 44 may read the corresponding computer program from the storage circuit independently.

For example, the term "processor" used in the above description refers to a central processing unit (CPU), a graphical processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements functions by reading and executing a computer program stored in the memory 41. Instead of storing a computer program in the memory 41, a computer program may also be directly embedded in a circuit of the processor. In this case, the processor implements the function by reading and executing a computer program embedded in the circuit.

In this example, the amount of contrast agent administered to the subject P differs depending on the weight. When the amount of contrast agent is not sufficient, an image of the subject P will not be accurate. When the amount of contrast agent is too much, a heavy burden will be placed on the kidneys. Moreover, the weight is used as one of the items to determine the intensity of X-rays with which the subject P is irradiated. However, the subject P may not be able to get on a weight scale due to injury or illness. Thus, the X-ray CT apparatus 1 is required to measure the accurate weight.

However, depending on the posture, position, or the like of the subject P placed on the table-top 33, different distortions occur in the table 30 by the weight of the subject P. Moreover, depending on the posture, position, or the like of the subject P placed on the table-top 33, different moment loads are applied to the table 30 by the weight of the subject P. That is, depending on the posture, position, or the like of the subject P placed on the table-top 33, there may be an error in the weight of the subject P measured by the table 30.

The operation function 441 receives a measurement operation of instructing the user to measure the weight of the subject P. The operation function 441 is an example of an operation unit. For example, the operation function 441 receives a measurement operation via an operation unit provided in the gantry 10, an operation unit provided in the table 30, the input interface circuitry 43, and the like.

Moreover, the operation function 441 may receive an operation at any timing. That is, the operation function 441 may receive a measurement operation before the table-top 33 is inserted into the gantry 10, while the table-top 33 is being inserted into the gantry 10, or while the gantry 10 is scanning the subject P.

The measurement signal acquisition function 442 acquires a measurement signal measured by the weight sensor 312. More specifically, the measurement signal acquisition function 442 acquires a measurement signal output from each of the weight sensors 312, when a measurement operation is received by the operation function 441. That is, the measurement signal acquisition function 442 acquires the current measurement signal.

The measurement mode acquisition function 443 acquires a measurement mode of the subject P placed on the table-top 33. The measurement mode acquisition function 443 is an example of a first acquisition unit. For example, the measurement mode includes posture information on the posture of the subject P placed on the table-top 33. Furthermore, the measurement mode may also include posture information and position information indicating the position of the table-top 33 on which the subject P is placed. That is, the measurement mode acquisition function 443 acquires the measurement mode including the posture information indicating the posture of the subject P placed on the table-top 33, and the position information indicating the position of the table-top 33 on which the subject P is placed.

For example, the measurement mode acquisition function 443 acquires the posture information indicating the direction of the subject P to be inserted into the gantry 10, such as head-first or feet-first. The measurement mode acquisition function 443 acquires the posture information from a scan plan. The scan plan is information in which the scan order and various conditions are set for the CT scan performed on the subject P. The scan plan includes information indicating the posture of the subject P to be scanned such as head-first or feet-first. Moreover, the scan plan may be referred to as an imaging protocol.

Moreover, the measurement mode acquisition function 443 may acquire the posture information on the posture of the subject P placed on the table-top 33, on the basis of a captured image of the subject P placed on the table-top 33 captured by an imaging device. For example, the measurement mode acquisition function 443 acquires the posture information of the subject P placed on the table-top 33, by detecting the head or feet of the subject P in the captured image. The captured image is an image in which the posture information and the position information on the subject P placed on the table-top 33 can be identified.

Furthermore, the measurement mode acquisition function 443 may acquire the posture information via the operation unit provided in the gantry 10, the operation unit provided in the table 30, the input interface circuitry 43, or the like. In this manner, the measurement mode acquisition function 443 may acquire the posture information by any method.

Still furthermore, the measurement mode acquisition function 443 acquires the measurement mode including the position information on the position of the subject P placed on the table-top 33. The position information is information indicating the position of the subject P in the X-axis direction, the Y-axis direction, and the Z-axis direction illustrated in FIG. 1. For example, the measurement mode acquisition function 443 acquires information indicating the current position of the table-top 33 from the controller 15 that controls the operation of the table 30. Still furthermore, the measurement mode acquisition function 443 estimates the position information indicating the position of the subject P, on the basis of information indicating the current position of the table-top 33. In this manner, the measurement mode acquisition function 443 estimates the position information indicating the position of the subject P.

Still furthermore, the measurement mode acquisition function 443 may acquire the position information on the position of the subject P placed on the table-top 33, on the basis of a captured image of the subject P placed on the table-top 33. That is, the measurement mode acquisition function 443 may acquire the position information on the position of the center of gravity of the subject P placed on the table-top 33 on the basis of the captured image. For example, the measurement mode acquisition function 443 detects a specific region of the subject P from the captured image. Then, the measurement mode acquisition function 443 may acquire the position information on the basis of the position of the specific region in the captured image.

Still furthermore, the measurement mode acquisition function 443 may acquire the position information via the operation unit provided in the gantry 10, the operation unit provided in the table 30, the input interface circuitry 43, or the like. In this manner, the measurement mode acquisition function 443 may acquire the position information by any method.

Moreover, the position information may be information indicating the position of the center of gravity of the subject P. That is, the measurement mode acquisition function 443 may acquire the measurement mode including the position information on the position of the center of gravity of the subject P placed on the table-top 33. For example, the measurement mode acquisition function 443 may acquire the measurement mode including the position information on the position of the center of gravity of the subject P placed on the table-top 33, on the basis of a captured image of the subject P placed on the table-top 33. Furthermore, the measurement mode acquisition function 443 may acquire the position information on the position of the center of gravity of the subject P via the operation unit provided in the gantry 10, the operation unit provided in the table 30, the input interface circuitry 43, or the like. The X-ray CT apparatus 1 can more accurately estimate the way of the distortions and how the moment load is applied, by acquiring the position information indicating the position of the center of gravity the subject P. Therefore, the measurement mode acquisition function 443 can improve the estimation accuracy of the weight of the subject P.

Still furthermore, the measurement mode acquisition function 443 may acquire other information, when other information other than the posture information and the position information is set as the measurement mode in the measurement-mode-based calibration information 411. The measurement mode acquisition function 443 may acquire physique information indicating the physique of the subject P, such as an adult or a child.

For example, the measurement mode acquisition function 443 may acquire the physique information via the operation unit provided in the gantry 10, the operation unit provided in the table 30, the input interface circuitry 43, or the like. Still furthermore, the measurement mode acquisition function 443 may acquire the physique information indicating the physique of the subject P placed on the table-top 33, from an image captured by the imaging device that captures the table-top 33 within the imaging range.

The measurement mode acquisition function 443 may acquire the measurement mode by using a trained model. For example, the measurement mode acquisition function 443 may acquire the measurement mode by inputting the captured image into the trained model that outputs the measurement mode included in the captured image, when the captured image captured by the imaging device is input.

For example, when a captured image captured by the imaging device is input, the trained model outputs the position information on the position of the center of gravity of the subject P placed on the table-top 33, and the posture information on the posture of the subject P placed on the table-top 33, included in the captured image. That is, the measurement mode acquisition function 443 may acquire the position information on the position of the subject P placed on the table-top 33, and the posture information indicating the direction of the subject P to be inserted into the gantry 10 for scanning the subject P, on the basis of the captured image indicating the measurement mode of the subject P placed on the table-top 33. Alternatively, when a captured image captured by the imaging device is input, the trained model may output the position information on the position of the center of gravity of the subject P placed on the table-top 33, the posture information on the posture of the subject P placed on the table-top 33, and the physique information indicating the physique of the subject P placed on the table-top 33 included in the captured image. That is, the measurement mode acquisition function 443 may acquire the position information on the position of the center of gravity of the subject P placed on the table-top 33, and the posture information indicating the direction of the subject P to be inserted into the gantry 10 for scanning the subject P, on the basis of the captured image indicating the measurement mode of the subject P placed on the table-top 33.

The calibration information acquisition function 444 acquires the calibration information corresponding to the measurement mode acquired by the measurement mode acquisition function 443, from the memory 41 that stores the measurement-mode-based calibration information 411 in which the calibration information for associating the measurement signal with the weight, and the measurement mode are associated with each other. The calibration information acquisition function 444 is an example of a second acquisition unit. That is, the calibration information acquisition function 444 acquires the calibration information associated with the measurement mode corresponding to the measurement mode acquired by the measurement mode acquisition function 443, from the measurement-mode-based calibration information 411.

Furthermore, when the measurement-mode-based calibration information 411 includes the physique information as a measurement mode, the calibration information acquisition function 444 may acquire the calibration information corresponding to the measurement mode corresponding to the measurement mode including the physique information acquired by the measurement mode acquisition function 443, from the measurement-mode-based calibration information 411.

In this process, the measurement mode acquired by the measurement mode acquisition function 443 may not match with the measurement mode of the measurement-mode-based calibration information 411. In such a case, the calibration information acquisition function 444 selects a measurement mode from the measurement modes in the measurement-mode-based calibration information 411. Then, the calibration information acquisition function 444 acquires the calibration information associated with the selected measurement mode, from the measurement-mode-based calibration information 411.

More specifically, the calibration information acquisition function 444 acquires the calibration information corresponding to a measurement mode approximated to the measurement mode acquired by the measurement mode acquisition function 443. For example, the position information on the measurement mode of the measurement-mode-based calibration information 411 may not match with the position information on the measurement mode acquired by the measurement mode acquisition function 443. In such a case, the calibration information acquisition function 444 acquires the calibration information corresponding to the position information closest to the position indicated by the position information on the measurement mode acquired by the measurement mode acquisition function 443, among the pieces of position information on the measurement mode in the measurement-mode-based calibration information 411. Alternatively, the calibration information acquisition function 444 receives an operation of selecting position information, among the pieces of position information on the measurement mode in the measurement-mode-based calibration information 411. Then, the calibration information acquisition function 444 may acquire the calibration information corresponding to the position information selected by the operation.

The same also applies to the posture information. For example, when the posture information on the measurement mode in the measurement-mode-based calibration information 411 does not match with the posture information on the measurement mode acquired by the measurement mode acquisition function 443, the calibration information acquisition function 444 acquires the calibration information corresponding to the posture information closest to the posture information on the measurement mode acquired by the measurement mode acquisition function 443, among the pieces of posture information on the measurement mode in the measurement-mode-based calibration information 411. Alternatively, the calibration information acquisition function 444 receives an operation of selecting posture information, among the pieces of posture information on the measurement mode in the measurement-mode-based calibration information 411. Then, the calibration information acquisition function 444 may acquire the calibration information corresponding to the posture information selected by the operation.

The same also applies to the physique information. For example, when the physique information on the measurement mode in the measurement-mode-based calibration information 411 does not match with the physique information on the measurement mode acquired by the measurement mode acquisition function 443, the calibration information acquisition function 444 acquires the calibration information corresponding to the physique information closest to the physique information on the measurement mode acquired by the measurement mode acquisition function 443, among the pieces of physique information on the measurement mode in the measurement-mode-based calibration information 411. Alternatively, the calibration information acquisition function 444 receives an operation of selecting physique information, among the pieces of physique information on the measurement mode in the measurement-mode-based calibration information 411. Then, the calibration information acquisition function 444 may acquire the calibration information corresponding to the physique information selected by the operation.

The weight estimation function 445 estimates the weight of the subject P placed on the table-top 33, on the basis of the measurement signal acquired by the measurement signal acquisition function 442 and the measurement mode of the subject P placed on the table-top 33. In this process, the calibration information acquisition function 444 acquires the calibration information corresponding to the measurement mode approximated to the measurement mode acquired by the measurement mode acquisition function 443. That is, the weight estimation function 445 estimates the weight of the subject P placed on the table-top 33, on the basis of the calibration information corresponding to the measurement mode and the measurement signal acquired by the measurement signal acquisition function 442. The weight estimation function 445 is an example of an estimation unit. More specifically, if there is a measurement signal that matches with the measurement signal acquired by the measurement signal acquisition function 442, the weight estimation function 445 estimates that the value associated with the matching measurement signal is the weight value.

If there is no measurement signal that matches with the measurement signal acquired by the measurement signal acquisition function 442, the weight estimation function 445 estimates the weight value by linear interpolation. The weight estimation function 445 estimates the weight of the subject P, on the basis of the value obtained by interpolating the calibration information acquired by the calibration information acquisition function 444 with linear interpolation, and the measurement signal measured by the weight sensor 312. More specifically, the weight estimation function 445 interpolates a function indicating the correspondence between the measurement signal and the weight value included in the calibration information with linear interpolation. Moreover, the weight estimation function 445 extracts the value corresponding to the measurement signal acquired by the measurement signal acquisition function 442, from the function indicating the correspondence between the measurement signal and the weight value. Then, the weight estimation function 445 estimates that the extracted value is the weight value of the subject P.

Moreover, if there is no measurement signal that matches with the measurement signal acquired by the measurement signal acquisition function 442, the weight estimation function 445 may also estimate that the value associated with the approximate measurement signal is the weight value. Furthermore, the weight estimation function 445 may estimate the weight value by other methods.

The output function 446 outputs the weight value estimated by the weight estimation function 445. That is, the output function 446 outputs the weight value of the subject P placed on the table-top 33. For example, the output function 446 outputs the weight value of the subject P by displaying the weight value on the display 42. Moreover, the output function 446 may also output the weight value of the subject P by other methods, in addition to displaying the weight value on the display 42.

Next, a process executed by the X-ray CT apparatus 1 will be described.

Figure 4:
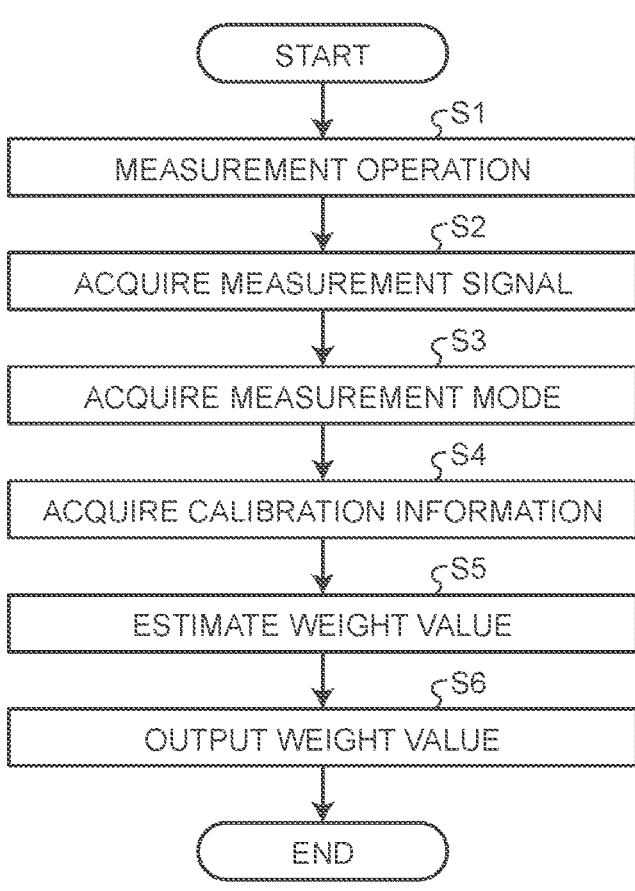
FIG. 4 is a flowchart illustrating an example of a measurement process executed by the X-ray CT apparatus according to the first embodiment.

FIG. 4 is a flowchart illustrating an example of a measurement process executed by the X-ray CT apparatus 1 according to the first embodiment.

The operation function 441 receives a measurement operation of instructing the user to measure the weight of the subject P placed on the table-top 33 (step S1).

The measurement signal acquisition function 442 acquires a measurement signal from the weight sensors 312 disposed on the table 30 (step S2).

The measurement mode acquisition function 443 acquires the measurement mode of the weight of the subject P placed on the table-top 33 (step S3).

The calibration information acquisition function 444 acquires the calibration information associated with the measurement mode corresponding to the measurement mode acquired by the measurement mode acquisition function 443, in the measurement-mode-based calibration information 411 (step S4).

The weight estimation function 445 estimates the weight value of the subject P placed on the table-top 33, on the basis of the measurement signal acquired by the measurement signal acquisition function 442 and the calibration information acquired by the calibration information acquisition function 444 (step S5).

The output function 446 outputs the weight value estimated by the weight estimation function 445 (step S6).

Accordingly, the X-ray CT apparatus 1 finishes the measurement process.

As described above, the X-ray CT apparatus 1 according to the first embodiment includes the table-top 33, the X-shaped link 311 that supports the table-top 33, and the weight sensor 312 placed on the table-top 33. The X-ray CT apparatus 1 acquires a measurement mode including the posture information on the posture of the subject P placed on the table-top 33. Moreover, the X-ray CT apparatus 1 obtains the calibration information corresponding to the measurement mode, from the memory 41 that stores the measurement-mode-based calibration information 411 in which the calibration information for associating the measurement signal with the weight, and the measurement mode are associated with each other. Then, the X-ray CT apparatus 1 estimates the weight of the subject P, on the basis of the calibration information and the measurement signal measured by the weight sensor 312. In this manner, the X-ray CT apparatus 1 estimates the weight of the subject P according to the measurement mode and the measurement signal. Therefore, the X-ray CT apparatus 1 can guarantee the measurement accuracy regardless of the measurement mode.

In this manner, even if the weight of the subject P is unknown, the X-ray CT apparatus 1 can obtain the weight of the subject P. Therefore, for example, the health care professional can determine the amount of contrast agent suitable for the subject P. Moreover, for example, the health care professional can determine the X-ray intensity suitable for the subject P.

Furthermore, the X-ray CT apparatus 1 can guarantee the measurement accuracy regardless of the measurement mode. Therefore, even if the table-top 33 on which the subject P is placed is inserted into the gantry 10, the X-ray CT apparatus 1 can measure the weight of the subject P without reducing the measurement accuracy. Hence, the X-ray CT apparatus 1 can measure the weight of the subject P while scanning the subject P.

Second Embodiment

The memory 41 of the X-ray CT apparatus 1 according to the first embodiment stores the measurement-mode-based calibration information 411. Then, the processing circuitry 44 estimates the weight of the subject P according to the measurement mode and the measurement signal, by using the measurement-mode-based calibration information 411.

Figure 5:
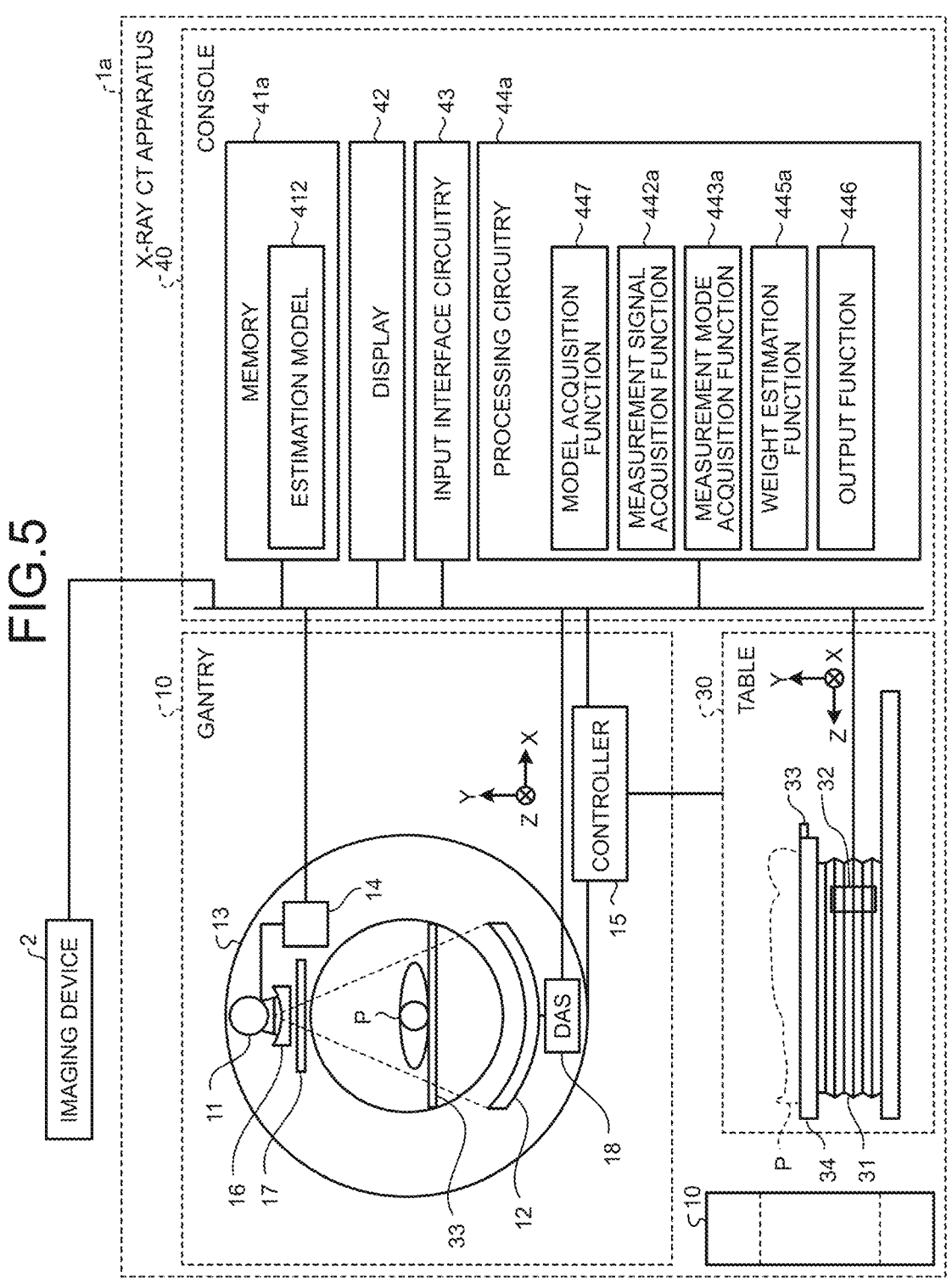
FIG. 5 is a diagram illustrating an example of a configuration of an X-ray CT apparatus according to a second embodiment.

An X-ray CT apparatus 1a according to a second embodiment estimates the weight of the subject P according to the measurement mode and the measurement signal, by using an estimation model 412. FIG. 5 is a diagram illustrating an example of a configuration of the X-ray CT apparatus 1a according to the second embodiment.

The X-ray CT apparatus 1a is connected to an imaging device 2. The imaging device 2 is a camera that captures an image of the subject P being placed on the table-top 33, in an examination room where the table 30 is installed. That is, the imaging device 2 captures a captured image that can identify the measurement mode of the subject P on the table-top 33. More specifically, the imaging device 2 captures a captured image indicating the posture of the subject P placed on the table-top 33 and the position of the table-top 33 on which the subject P is placed.

The X-ray CT apparatus 1a may also be connected to a plurality of the imaging devices 2 in addition to a single imaging device 2. Then, the imaging devices 2 may each capture a captured image from the position where each of the imaging devices 2 is installed.

A memory 41a stores the estimation model 412. The estimation model 412 is a trained model that outputs the weight of the subject P, when the captured image captured by the imaging device 2 and the measurement value indicated by the measurement signal of the weight sensor 312 are input. For example, in a training stage, when various combinations of the captured image indicating the posture and position of the subject P on the table-top 33, the measurement signals of the weight sensors 312, and the weight of the subject P are input, the estimation model 412 trains the weight of the subject P according to the captured image and the measured signal. That is, the estimation model 412 is trained by a plurality of pieces of training data with different combinations of the subject P placed on the table-top 33, the posture of the subject P on the table-top 33, and the position of the subject P on the table-top 33. In this manner, the estimation model 412 is generated.

For example, processing circuitry 44a includes a model acquisition function 447, the operation function 441, a measurement signal acquisition function 442a, a measurement mode acquisition function 443a, a weight estimation function 445a, and the output function 446.

The model acquisition function 447 acquires the estimation model 412. For example, the model acquisition function 447 acquires the estimation model 412 from an apparatus connected via a network. The model acquisition function 447 stores the acquired estimation model 412 in the memory 41*a*.

The measurement signal acquisition function 442*a* acquires a measurement signal indicating the value of each of the measurement signals measured by the weight sensors 312.

The measurement mode acquisition function 443*a* acquires a captured image captured by the imaging device 2 and that indicates the measurement mode of the subject P placed on the table-top 33. The measurement mode acquisition function 443*a* is an example of a first acquisition unit. More specifically, the measurement mode acquisition function 443*a* acquires a captured image captured when the measurement signal is acquired by the measurement signal acquisition function 442*a*.

When the measurement signal of each of the weight sensors 312 acquired by the measurement signal acquisition function 442*a* and the measurement mode are input, the weight estimation function 445*a* estimates the weight of the subject P by the estimation model 412 that outputs the weight of the subject P placed on the table-top 33. That is, when the measurement signal of each of the weight sensors 312 acquired by the measurement signal acquisition function 442*a* and the captured image acquired by the measurement mode acquisition function 443*a* are input, the weight estimation function 445*a* estimates the weight of the subject P, by the estimation model 412 that outputs the weight of the subject P placed on the table-top 33. Specifically, when the measurement signal and the captured image are input into the estimation model 412, the weight estimation function 445*a* estimates that the value output from the estimation model 412 is the weight of the subject P.

The output function 446 outputs the weight estimated by the weight estimation function 445. For example, the output function 446 displays the weight estimated by the weight estimation function 445 on the display 42.

As described above, the X-ray CT apparatus 1*a* according to the second embodiment acquires a captured image indicating the measurement mode of the subject P placed on the table-top 33. Moreover, the X-ray CT apparatus 1*a* inputs the measurement signal and the captured image into the estimation model 412 that outputs the weight of the subject P placed on the table-top 33. Then, the X-ray CT apparatus 1*a* estimates that the value output from the estimation model 412 is the weight of the subject P. In this manner, the X-ray CT apparatus 1*a* estimates the weight of the subject P according to the measurement mode and the measurement signal. Therefore, the X-ray CT apparatus 1*a* can guarantee the measurement accuracy regardless of the measurement mode.

The estimation model 412 may also estimate the weight of the subject P, when an article to be placed is placed on the table-top 33 in addition to the subject P. The article to be placed is an article to be placed on the table-top 33 with the subject P. The article to be placed is an article that supports the CT scan performed on the subject P, an article that cannot be removed from the subject P, or the like. For example, the article to be placed is a mattress for supporting and maintaining the posture of the subject P, an infusion instrument used to deliver medications such as contrast agents to the subject P, a urine bag for collecting urine discharged from the subject P, and the like.

In this example, when an article to be placed is placed on the table-top 33, the measurement signal of each of the weight sensors 312 differs depending on the position where the article to be placed is placed, and the weight of the article to be placed. Thus, the estimation model 412 may also estimate the weight of the subject P, by including the fact that an article to be placed is placed on the table-top 33 in the calculation.

For example, the measurement mode acquisition function 443*a* acquires a captured image indicating the measurement mode that can identify the posture of the subject P on the table-top 33, the position of the subject P on the table-top 33, the type of an article to be placed on the table-top 33, and the position of the article to be placed on the table-top 33. When the captured image and the measurement signal are input, the weight estimation function 445*a* estimates the weight of the subject P by the estimation model 412 that outputs the weight of the subject P placed on the table-top 33. That is, the weight estimation function 445*a* inputs the captured image and the measurement signal into the estimation model 412. When the captured image captured by the imaging device 2 and the measurement value indicated by the measurement signal of the weight sensor 312 are input, the estimation model 412 outputs the weight of the subject P. More specifically, the captured image that can identify the posture of the subject P on the table-top 33, the position of the subject P on the table-top 33, the type of an article to be placed on the table-top 33, and the position of the article to be placed on the table-top 33 is input into the estimation model 412. Moreover, while the article to be placed is placed on the table-top 33, the measurement signal measured by the weight sensor 312 is input into the estimation model 412. Then, the estimation model 412 outputs the weight of the subject P that does not include the weight of the article to be placed that is placed on the table-top 33.

For example, in a training stage, when various combinations of the captured image that can identify the posture and position of the subject P on the table-top 33 and the type and position of an article to be placed on the table-top 33, the measurement signal of each of the weight sensors 312, and the weight of the subject P are input, the estimation model 412 trains the weight of the subject P according to the captured image and the measurement signal. That is, the estimation model 412 is trained by a plurality of pieces of training data with different combinations of the subject P placed on the table-top 33, the posture of the subject P on the table-top 33, the position of the subject P on the table-top 33, the type of an article to be placed on the table-top 33, and the position of the article to be placed on the table-top 33. In this manner, the estimation model 412 is generated.

Moreover, the model acquisition function 447 may have a training function to train the estimation model 412. For example, the model acquisition function 447 trains the estimation model 412, by inputting the measurement signals of the weight sensors 312, the captured image indicating the measurement mode of the subject P acquired by the measurement mode acquisition function 443*a*, and various combinations of the measurement signal and the weight of the subject P in the captured image, into the estimation model 412. The model acquisition function 447 is an example of a training unit. In this way, the model acquisition function 447 may acquire the estimation model 412, by generating the estimation model 412.

First Modification

Figure 6:
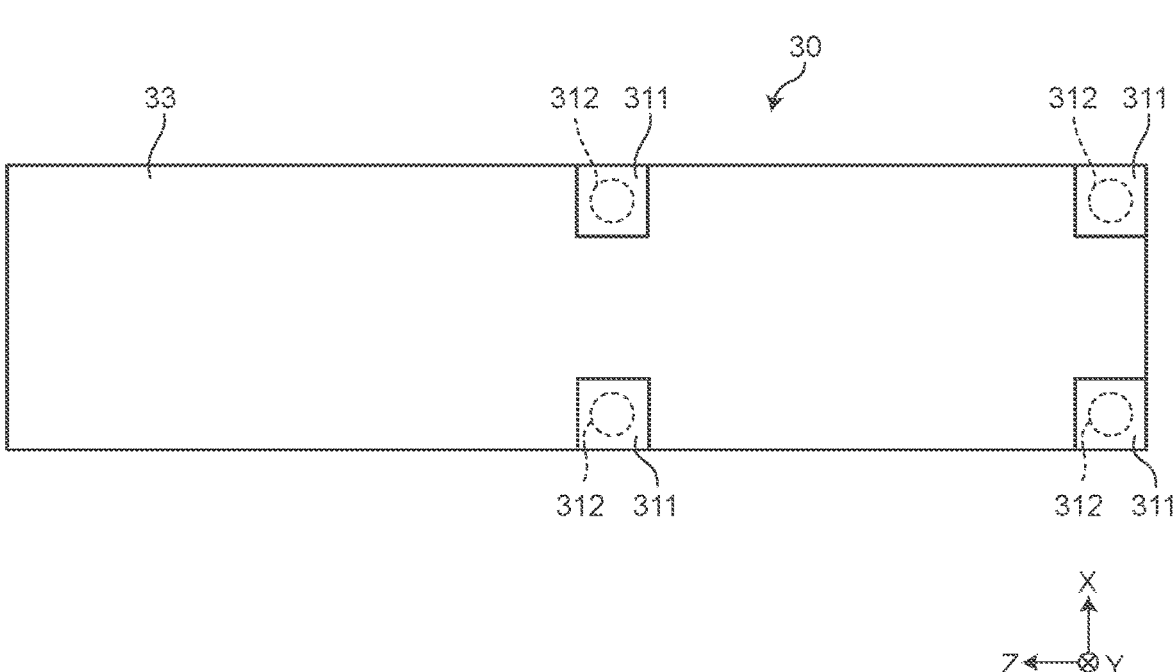
FIG. 6 is a diagram illustrating an example of an arrangement of weight sensors included in the table according to the first embodiment.

In the first embodiment and the second embodiment, the table 30 includes the weight sensor 312 between the table-top 33 and the X-shaped link 311. FIG. 6 is a diagram illustrating an example of an arrangement of the weight sensors 312 included in the table 30 according to the first embodiment. As illustrated in FIG. 6, the table 30 includes four weight sensors 312 between the table-top 33 and the X-shaped link 311. That is, the weight sensor 312 is disposed between the table-top 33 and the X-shaped link 311, and at the four corners of the X-shaped link 311.

Figure 7:
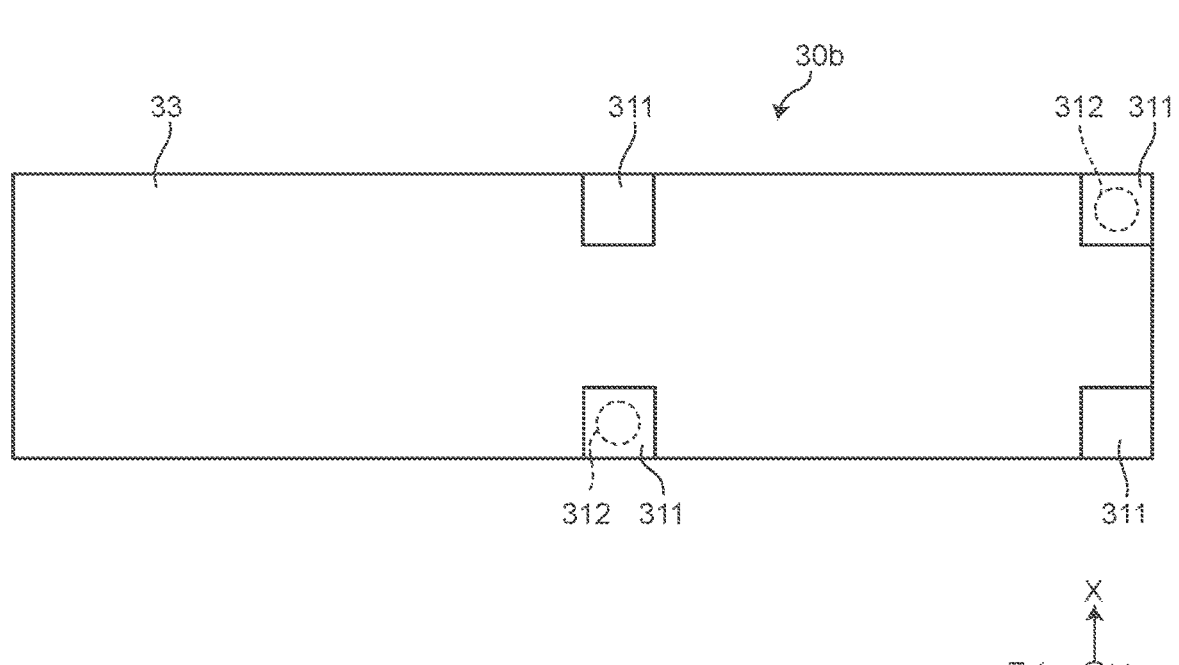
FIG. 7 is a diagram illustrating an example of an arrangement of weight sensors included in a table according to a first modification.

However, a table 30*b* may include four or less weight sensors 312. FIG. 7 is a diagram illustrating an example of an arrangement of the weight sensors 312 included in the table 30*b* according to a first modification. For example, as illustrated in FIG. 7, the X-shaped link 311 supports the table-top 33 at four locations. Then, these four locations form a rectangle by being connected by a line. The weight sensors 312 are disposed at two locations on a diagonal of the rectangle. More specifically, the weight sensors 312 are disposed between the table-top 33 and the X-shaped link 311, and on a diagonal connecting two of the four corners of the X-shaped link 311. In this manner, by reducing the number of the weight sensors 312, the table 30*b* can reduce the manufacturing cost.

Second Modification

Figure 8:
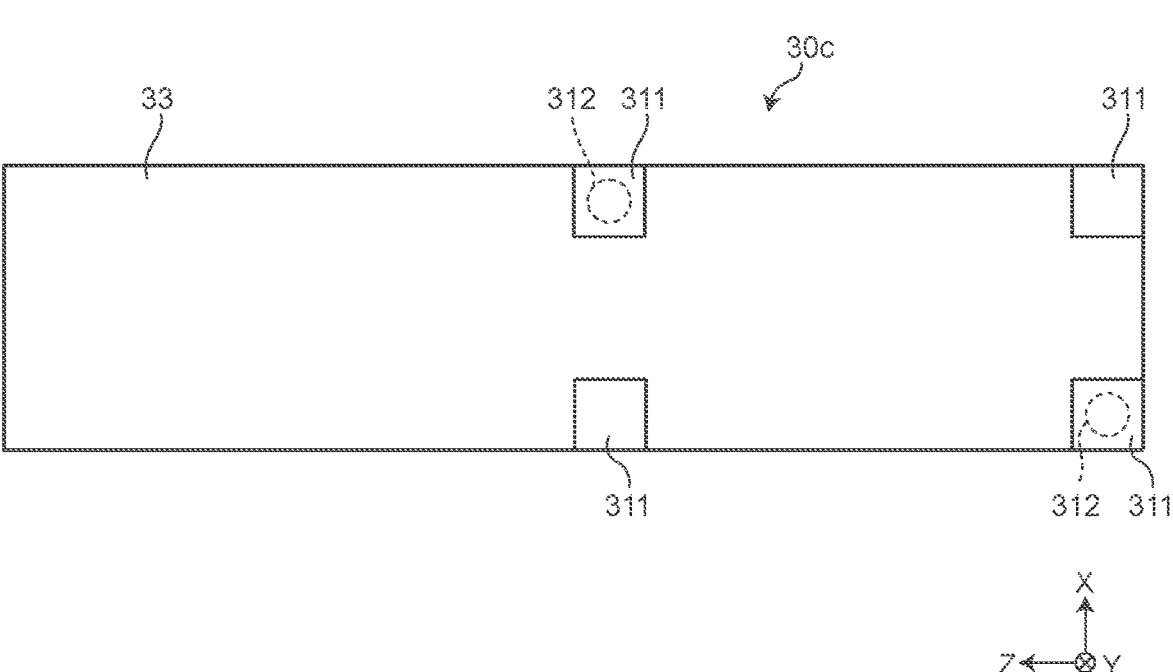
FIG. 8 is a diagram illustrating an example of an arrangement of weight sensors included in a table according to a second modification.

FIG. 8 is a diagram illustrating an example of an arrangement of the weight sensors 312 included in a table 30*c* according to a second modification. As illustrated in FIG. 8, the weight sensor 312 may also be disposed on two locations on another diagonal different from that according to the first modification. That is, the weight sensor 312 is disposed on two locations at the corners on the diagonal different from that according to the first modification.

Third Modification

In the first embodiment, the second embodiment, and first and second modifications for each embodiment, the measurement mode acquisition functions 443 and 443*a* may acquire the position information on the position of the center of gravity of the subject P placed on the table-top 33 on the basis of the measurement signal of each of the measurement sensors 312 and arrangement information on arrangement of each of the weight sensors 312. In this case, the X-ray CT apparatuses 1 and 1*a* may not include the imaging device 2. The arrangement information is information indicating arrangement of each of the weight sensors 312 on the tables 30, 30*b*, and 30*c*. The arrangement information is, for example, information indicating XY coordinates of each of the weight sensors 312 on a plane substantially parallel to the table-top 33.

When, for example, the weight sensors 312 are arranged at four corners of the X-shaped link 311 as illustrated in FIG. 6, the measurement mode acquisition functions 443 and 443*a* acquire the position information on the position of the center of gravity of the subject P placed on the table-top 33 by comparing measurement values indicated by the measurement signals of the four measurement sensors 312. In other words, the measurement mode acquisition functions 443 and 443*a* acquire the position information on the position of the center of gravity of the subject P placed on the table-top 33 on the basis of the measurement signals of the four measurement sensors 312 and the arrangement information indicating that the weight sensors 312 are arranged at the four corners.

When, for example, the weight sensors 312 are arranged on a diagonal connecting two of the four corners of the X-shaped link 311 as illustrated in FIG. 7 or 8, the measurement mode acquisition functions 443 and 443*a* acquire the position information on the position of the center of gravity of the subject P placed on the table-top 33 by comparing measurement values indicated by the measurement signals of the two measurement sensors 312. In other words, the measurement mode acquisition functions 443 and 443*a* acquire the position information on the position of the center of gravity of the subject P placed on the table-top 33 on the basis of the measurement signals of the two measurement sensors 312 and the arrangement information indicating that the weight sensors 312 are arranged on a diagonal connecting the two of the four corners.

Moreover, the calibration information acquisition function 444 acquires a piece of calibration information corresponding to, among the pieces of position information on the measurement mode included in the measurement-mode-based calibration information 411, a piece of position information indicating a position closest to the position indicated by the piece of information position acquired by the measurement mode acquisition functions 443 and 443*a*. The weight estimation functions 445 and 445*a* then estimate the weight of the subject P placed on the table-top 33, on the basis of the piece of calibration information acquired and the measurement signal acquired by the measurement signal acquisition function 442.

Figure 9:
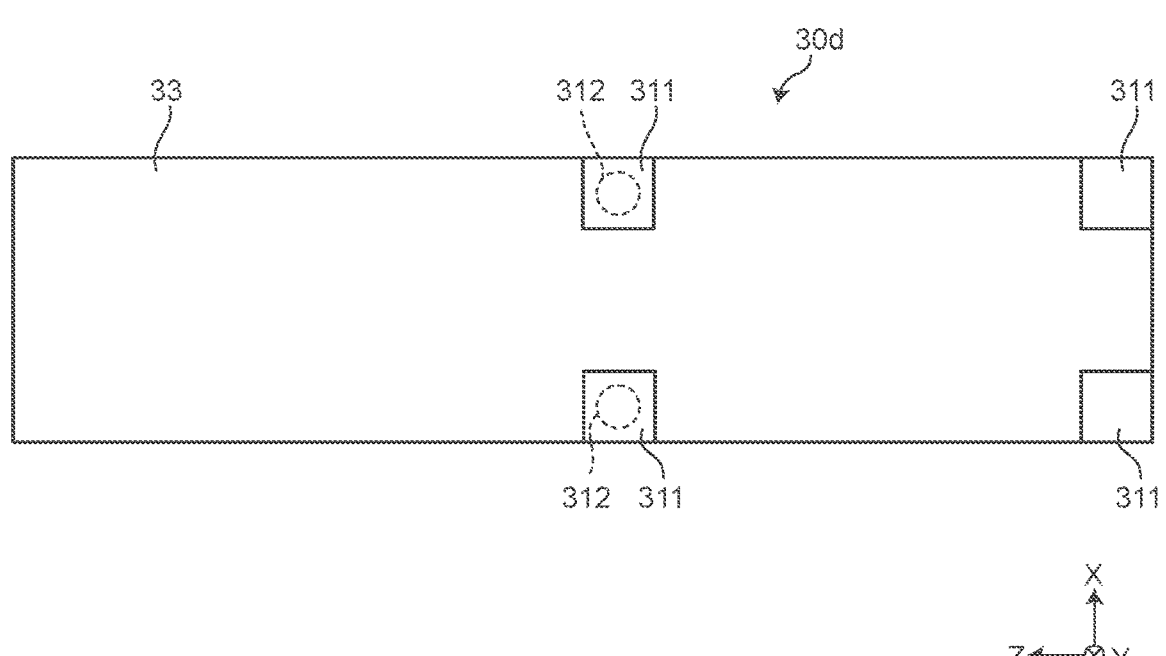
FIG. 9 is a diagram illustrating an example of an arrangement of weight sensors included in a table according to a third modification.

Note that the weight estimation functions 445 and 445*a* may estimate the weight of the subject P placed on the table-top 33 by a trained model. Upon receiving the measurement signal of each of the weight sensors 312 and the arrangement information indicating arrangement of each of the weight sensors 312, the weight estimation functions 445 and 445*a* may estimate the weight of the subject P placed on the table-top 33 by a trained model that outputs the weight of the subject P placed on the table-top 33. Fourth Modification FIG. 9 is a diagram illustrating an example of an arrangement of the weight sensors 312 included in a table 30*d* according to a third modification. For example, the X-shaped link 311 supports the table-top 33 at four locations. Then, these four locations form a rectangle by being connected by a line. The weight sensors 312 are disposed on two locations in the rectangle where the sides on the gantry 10 side are connected. More specifically, the weight sensors 312 are disposed between the table-top 33 and the X-shaped link 311, and are disposed side by side in the short direction of the table-top 33 among the four corners of the X-shaped link 311. For example, the weight sensors 312 are disposed on the apex of the two locations where the sides on the gantry 10 side are connected.

Fifth Modification

Figure 10:
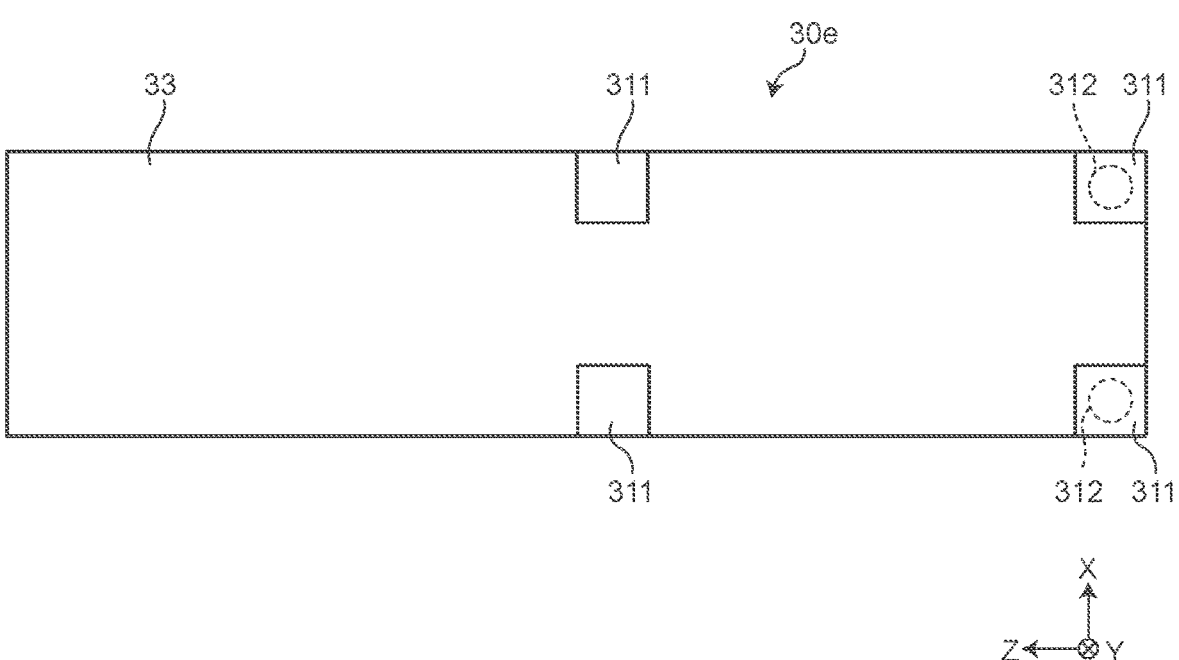
FIG. 10 is a diagram illustrating an example of an arrangement of weight sensors included in a table according to a fourth modification.

FIG. 10 is a diagram illustrating an example of an arrangement of the weight sensors 312 included in a table 30*e* according to a fourth modification. As illustrated in FIG. 10, the weight sensors 312 may be disposed on two locations where the sides opposite to those according to the third modification are connected. That is, the weight sensors 312 are disposed on the apex of the two locations where the sides opposite to those of the gantry 10 side are connected.

Sixth Modification

Figure 11:
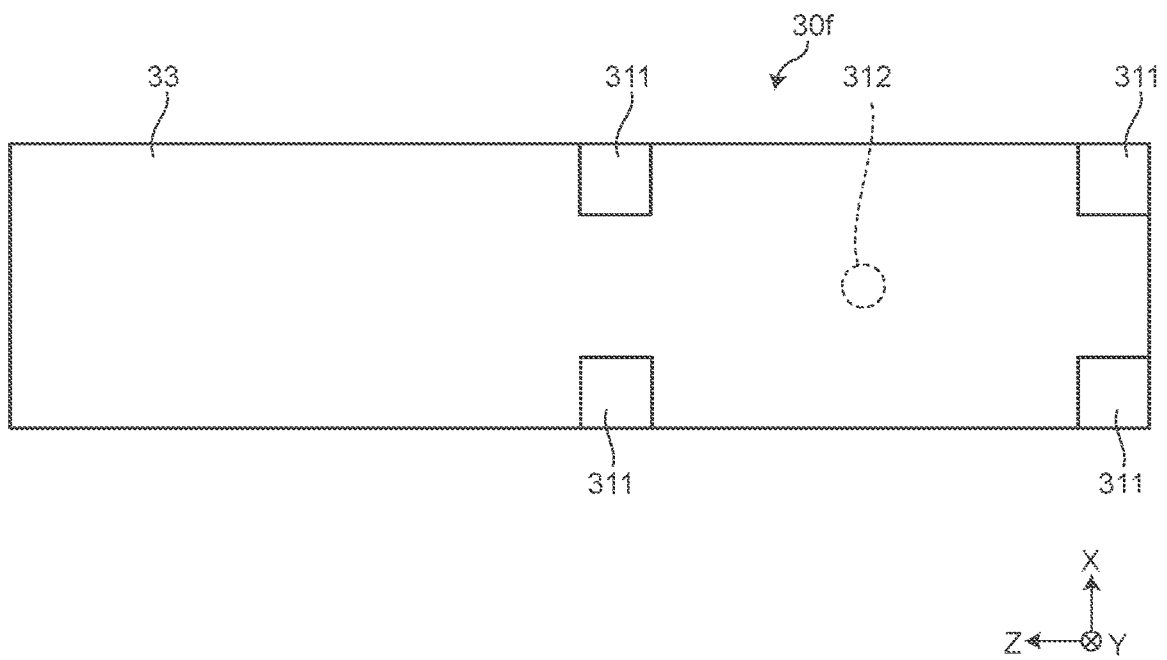
FIG. 11 is a diagram illustrating an example of an arrangement of a weight sensor included in a table according to a fifth modification.

FIG. 11 is a diagram illustrating an example of an arrangement of the weight sensor 312 included in a table 30*f* according to a fifth modification. As illustrated in FIG. 11, the weight sensor 312 may be disposed on a position different from the apex of a rectangle obtained by connecting the four locations of the X-shaped link 311 that support the table-top 33. The weight sensor 312 is disposed between the table-top 33 and the X-shaped link 311, and inside the four corners of the X-shaped link 311. More specifically, the weight sensor 312 is disposed substantially at the center of the table-top 33 in the short direction. In other words, the weight sensor 312 is disposed substantially at the center of the rectangle obtained by connecting the four locations of the X-shaped link 311 that support the table-top 33.

Seventh Modification

In the X-ray CT apparatus 1 according to the first embodiment, the console 40 includes the operation function 441, the measurement signal acquisition function 442, the measurement mode acquisition function 443, the calibration information acquisition function 444, the weight estimation function 445, and the output function 446. In the X-ray CT apparatus 1a according to the second embodiment, the console 40 includes the operation function 441, the measurement signal acquisition function 442a, the weight estimation function 445a, the output function 446, and the model acquisition function 447. However, the table 30 may also include all or part of the operation function 441, the measurement signal acquisition function 442 or 442a, the measurement mode acquisition function 443, the calibration information acquisition function 444, the weight estimation function 445 or 445a, the output function 446, and the model acquisition function 447.

For example, the table 30 includes processing circuitry and a memory. In the table 30, the functions are stored in the memory in the form of a computer executable program. The processing circuitry is a processor that reads and executes a computer program from the memory, and implements the function corresponding to each computer program. Then, the processing circuitry that has read out computer programs has the operation function 441, the measurement signal acquisition function 442, the measurement mode acquisition function 443, the calibration information acquisition function 444, the weight estimation function 445, the output function 446, and the model acquisition function 447. Moreover, the table 30 may store the measurement-mode-based calibration information 411 and the estimation model 412, or may acquire the measurement-mode-based calibration information 411 and the estimation model 412 stored in other device.

Eighth Modification

The table 30 according to the first embodiment and the second embodiment includes the weight sensors 312 between the table-top 33 and the X-shaped link 311. However, the weight sensor 312 may also be provided in other locations.

More specifically, the weight sensor 312 may be disposed between the upper surface of the table-top 33 and the upper surface of the floor surface. For example, the weight sensor 312 may be disposed between the table-top 33 and the X-shaped link 311 for movably supporting the table-top 33. More specifically, the weight sensor 312 may be disposed between the table-top 33 and the support frame 34, or may be disposed between the support frame 34 and the X-shaped link 311. Moreover, the weight sensor 312 may be disposed at any position inside the X-shaped link 311.

Figure 12:
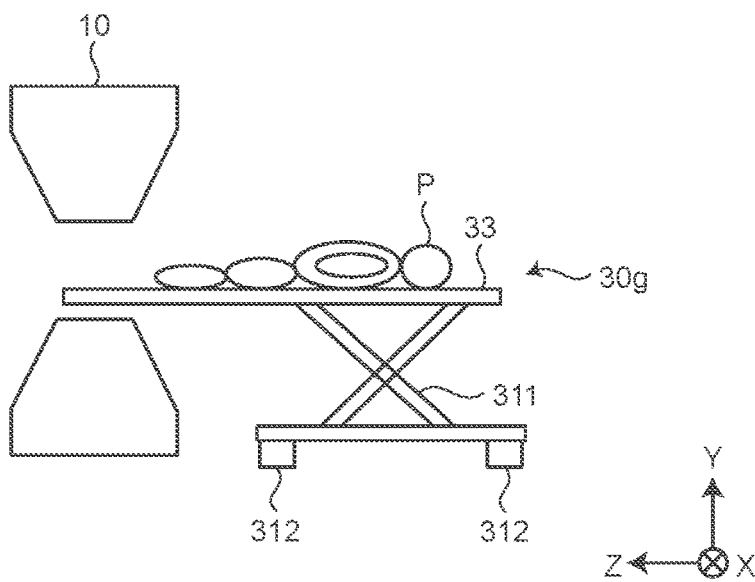
FIG. 12 is a diagram illustrating an example of a schematic configuration of the inside of a table according to a seventh modification.

Furthermore, the weight sensor 312 may be disposed between the X-shaped link 311 and the floor surface. FIG. 12 is a diagram illustrating an example of a schematic configuration of the inside of a table 30g according to a seventh modification. As illustrated in FIG. 12, the weight sensor 312 may be disposed between the X-shaped link 311 for movably supporting the table-top 33, and the floor surface.

Ninth Modification

In the first embodiment and the second embodiment, a medical image diagnostic apparatus is applied to the X-ray CT apparatus 1. However, it is not limited thereto, and the medical image diagnostic apparatus may also be applied to other apparatuses such as an X-ray diagnostic apparatus, a Magnetic Resonance Imaging (MRI) apparatus, a Single Photon Emission Computed Tomography (SPECT) apparatus, a Positron Emission computed Tomography (PET) apparatus, and the like, in addition to the X-ray CT apparatus 1.

Tenth Modification

The table 30, 30b, 30c, 30d, 30e, 30f, or 30g according to the first embodiment, the second embodiment, the first modification, the second modification, the third modification, the fourth modification, the fifth modification, the sixth modification, the seventh modification, and the eighth modification includes the X-shaped link 311 that supports, lifts, and lowers the table-top 33 inside the base 31. However, it is not limited thereto, and the table-top 33 of the table 30, 30b, 30c, 30d, 30e, 30f, or 30g may also be supported, lifted, and lowered by other mechanism, in addition to the X-shaped link 311. For example, the table-top 33 of the table 30, 30b, 30c, 30d, 30e, 30f, or 30g may be supported, lifted, and lowered by a parallel link mechanism in which the links of the same lengths are disposed in parallel, or may be supported, lifted, and lowered by the other mechanism.

According to at least one of the embodiments described above and the like, it is possible to guarantee the measurement accuracy regardless of the measurement mode.

The following notes are disclosed with respect to the above-mentioned embodiments as one of aspects and selectable features of the invention.

Note 1.

A medical image diagnostic apparatus, including:

a table-top on which a subject is placed;

a support unit that movably supports the table-top;

a measurement unit that measures a measurement signal corresponding to weight of the subject placed on the table-top; and processing circuitry configured to acquire a measurement mode including posture information on a posture of the subject placed on the table-top;

acquire from a memory a piece of calibration information corresponding to the measurement mode acquired, the memory storing information in which pieces of calibration information for associating a measurement signal with weight, and measurement modes are associated with each other; and estimate the weight of the subject based on the piece of the calibration information acquired and the measurement signal measured by the measurement unit.

Note 2.

The processing circuitry may also acquire the measurement mode including position information on a position of the subject placed on the table-top, and the processing circuitry may acquire from the memory a piece of the calibration information corresponding to the measurement mode including the posture information and the position information acquired.

Note 3.

The processing circuitry may also acquire the position information based on a captured image of the subject placed on the table-top.

Note 4.

The processing circuitry may also acquire the measurement mode including the position information on a position of a center of gravity of the subject placed on the table-top.

Note 5.

The processing circuitry may also acquire the posture information indicating a direction of the subject to be inserted into a gantry.

21

Note 6.

The measurement unit may also be a weight sensor that is disposed between the table-top and the support unit, and that measures weight of an object placed on the table-top.

Note 7.

The measurement unit may also be a weight sensor that is disposed between the support unit and a floor surface, and that measures weight of an object placed on the table-top.

Note 8.

The processing circuitry may also acquire the measurement mode including position information on a position of the subject placed on the table-top, and when any position information that matches with the position information on the measurement mode acquired is not stored in the memory, the processing circuitry may acquire from the memory a piece of the calibration information corresponding to position information close to a position indicated by the position information on the measurement mode acquired.

Note 9.

A table, including:

a table-top on which a subject is placed;

a support unit that movably supports the table-top;

a measurement unit that measures a measurement signal corresponding to weight of the subject placed on the table-top; and processing circuitry configured to acquire a measurement mode including posture information on a posture of the subject placed on the table-top;

acquire from a memory a piece of calibration information corresponding to the measurement mode acquired, the memory storing information in which pieces of calibration information for associating a measurement signal with weight, and measurement modes are associated with each other; and estimate the weight of the subject based on the piece of the calibration information acquired and the measurement signal measured by the measurement unit.

Note 10.

A control method of a medical image diagnostic apparatus that includes a table-top on which a subject is placed, a support unit for movably supporting the table-top, and a measurement unit that outputs a measurement signal corresponding to weight of the subject on the table-top, the control method including:

acquiring a measurement mode including posture information on a posture of the subject placed on the table-top;

acquiring from a memory a piece of calibration information corresponding to the acquired measurement mode, the memory storing information in which pieces of calibration information for associating a measurement signal with weight, and measurement modes are associated with each other; and estimating the weight of the subject based on the acquired piece of the calibration information and the measurement signal measured by the measurement unit.

Note 11.

A medical image diagnostic apparatus, including:

a table-top on which a subject is placed;

a measurement unit that outputs a measurement signal corresponding to weight of the subject placed on the table-top; and processing circuitry configured to estimate the weight of the subject placed on the table-top based on the measurement signal and arrangement information on arrangement of the measurement unit.

Note 12.

When the measurement signal and the arrangement information are input, the processing circuitry may also estimate the weight of the subject, by a trained model that outputs the weight of the subject placed on the table-top.

Note 13.

The processing circuitry may also acquire a captured image indicating the measurement mode of the subject placed on the table-top, and when the measurement signal and the captured image are input, the processing circuitry may also estimate the weight of the subject, by a trained model that outputs the weight of the subject placed on the table-top.

Note 14.

The processing circuitry may train the trained model by inputting the measurement signal, the captured image, and various combinations of the measurement signal and the weight of the subject in the captured image, into the trained model.

Note 15.

There may be further provided a memory that stores information in which pieces of calibration information for associating a measured signal with weight, and measurement modes are associated with each other.

The processing circuitry may acquire from the memory a piece of the calibration information corresponding to the measurement mode acquired, and the processing circuitry may estimate the weight of the subject based on the piece of the calibration information acquired and the measurement signal measured by the measurement unit.

Note 16.

The processing circuitry may also acquire the measurement mode including posture information on a posture of the subject placed on the table-top, and position information on a position of the subject, and the processing circuitry may also acquire from the memory a piece of the calibration information corresponding to the measurement mode including the posture information and the position information acquired.

Note 17.

The processing circuitry may also acquire the position information on the position of the subject placed on the table-top, based on a captured image indicating the measurement mode of the subject placed on the table-top.

Note 18.

The processing circuitry may also acquire the position information on a position of the center of gravity of the subject placed on the table-top, based on a captured image indicating the measurement mode of the subject placed on the table-top.

Note 19.

The processing circuitry may also acquire the posture information indicating a direction of the subject to be inserted into a gantry that scans the subject.

Note 20.

The measurement unit may also be a weight sensor that is disposed between the table-top and the support unit for movably supporting the table-top, and that measures weight of an object placed on the table-top.

Note 21.

The measurement unit may also be a weight sensor that is disposed between the support unit for movably supporting the table-top and a floor surface, and that measures weight of an object placed on the table-top.

Note 22.

The processing circuitry may also acquire the measurement mode including position information on a position of the subject placed on the table-top, and when any position information that matches with the position information on the measurement mode acquired is not stored in the memory, the processing circuitry may acquire from the memory a piece of the calibration information corresponding to position information close to a position indicated by the position information on the measurement mode acquired.

Note 23.

A table, including:

a table-top on which a subject is placed;

a support unit that movably supports the table-top;

a measurement unit that outputs a measurement signal corresponding to weight of the subject placed on the table-top; and processing circuitry configured to acquire a measurement mode of the subject placed on the table-top; and estimate the weight of the subject placed on the table-top based on the measurement signal and the measurement mode.

Note 24.

A control method of a medical image diagnostic apparatus that includes a table-top on which a subject is placed, a support unit that movably supports the table-top, and a measurement unit that outputs a measurement signal corresponding to weight of the subject placed on the table-top, the control method including:

acquiring a measurement mode of the subject placed on the table-top; and estimating the weight of the subject placed on the table-top based on the measurement signal and the measurement mode.

Note 25.

The processing circuitry may receive a measurement operation for instruction to measure the weight of the subject.

Note 26.

The processing circuitry may also acquire the posture information indicating a direction of the subject to be inserted into the gantry, from a scan plan of scanning the subject by the gantry.

Note 27.

The processing circuitry may also acquire the posture information on the posture of the subject placed on the table-top, based on a captured image indicating the measurement mode of the subject placed on the table-top.

Note 28.

The processing circuitry may also acquire the measurement mode including physique information indicating physique of the subject placed on the table-top, and the processing circuitry may also estimate the weight of the subject placed on the table-top, based on the measurement signal and the measurement mode including the physique information.

Note 29.

The processing circuitry may output a weight value of the subject placed on the table-top.

Note 30.

The processing circuitry may also output the weight value of the subject placed on the table-top, by displaying the weight value on a display unit.

Note 31.

When any measurement signal that matches with a measurement signal acquired is not included, the processing circuitry may estimate the weight of the subject, based on a value obtained by interpolating the piece of the calibration information acquired with a linear interpolation, and the measurement signal.

Note 32.

The processing circuitry may acquire a captured image indicating the measurement mode that can identify the posture of the subject on the table-top, the position of the subject on the table-top, a type of an article on the table-top, and the position of the article on the table-top, and when the captured image and the measured signal are input, the processing circuitry may estimate the weight of the subject, by a trained model that outputs the weight of the subject placed on the table-top.

Note 33.

The measurement unit may be disposed between the table-top and the support unit, and at four corners of the support unit.

Note 34.

The measurement unit may be disposed between the table-top and the support unit, and on a diagonal connecting two of the four corners of the support unit.

Note 35.

The measurement unit may be disposed between the table-top and the support unit, and disposed side by side in a short direction of the table-top, among the four corners of the support unit.

Note 36.

The measurement unit may be disposed between the table-top and the support unit, and inside the four corners of the support unit.

Note 37.

A medical image diagnostic apparatus including:

a table-top on which a subject is placed;

a support unit that movably supports the table-top;

a measurement unit that outputs a measurement signal corresponding to weight of the subject placed on the table-top; and processing circuitry configured to acquire a measurement mode of the subject placed on the table-top; and estimate the weight of the subject placed on the table-top based on the measurement signal and the measurement mode.

Note 38.

When the measurement signal and the measurement mode are input, the processing circuitry may estimate the weight of the subject by a trained model that outputs the weight of the subject placed on the table-top.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
a table-top configured to place thereon a subject;
a plurality of measurement units that outputs a set of first measurement signals corresponding to weight of the subject placed on the table-top; and
processing circuitry configured to
acquire a first measurement mode indicating a mode for measuring the weight of the subject placed on the table-top; and
estimate the weight of the subject placed on the table-top by acquiring from a memory a weight value corresponding to the first measurement mode and the set of the respective first measurement signals of the plurality of measurement units, the memory storing second measurement modes each indicating a mode for measuring weight of a subject, sets of respective second measurement signals of the plurality of measurement units, and weight values associated with each other.

2. The medical image diagnostic apparatus according to claim 1, wherein
the memory stores pieces of calibration information and the second measurement modes associated with each other, the pieces of calibration information associating the sets of the respective second measurement signals of the plurality of measurement units with the weight values, and
the processing circuitry
acquires from the memory a piece of the calibration information corresponding to the acquired first measurement mode, and
estimates the weight of the subject, based on the acquired piece of the calibration information and the set of the respective first measurement signals of the plurality of measurement units.

3. The medical image diagnostic apparatus according to claim 2, wherein
the processing circuitry
acquires the first measurement mode including posture information on a posture of the subject placed on the table-top and position information on a position of the subject, and
acquires from the memory a piece of the calibration information corresponding to the acquired first measurement mode including the posture information and position information.

4. The medical image diagnostic apparatus according to claim 3, wherein the processing circuitry acquires the position information on the position of the subject placed on the table-top, based on a captured image indicating the first measurement mode of the subject placed on the table-top.

5. The medical image diagnostic apparatus according to claim 3, wherein the processing circuitry acquires the position information on a position of a center of gravity of the subject placed on the table-top, based on a captured image indicating the first measurement mode of the subject placed on the table-top.

6. The medical image diagnostic apparatus according to claim 3, wherein the processing circuitry acquires the posture information indicating a direction of the subject to be inserted into a gantry that scans the subject, based on a captured image indicating the first measurement mode of the subject placed on the table-top.

7. The medical image diagnostic apparatus according to claim 2, wherein
the processing circuitry
acquires the first measurement mode including position information on a position of the subject placed on the table-top, and
when any position information that matches with the position information on the acquired first measurement mode is not stored in the memory, acquires from the memory a piece of the calibration information corresponding to position information close to a position indicated by the position information of the acquired first measurement mode.

8. The medical image diagnostic apparatus according to claim 1, wherein each of the plurality of measurement units is a weight sensor that is disposed between the table-top and a support unit for supporting the table-top, and that measures weight of an object placed on the table-top.

9. The medical image diagnostic apparatus according to claim 1, wherein each of the plurality of measurement units is a weight sensor that is disposed between a support unit for supporting the table-top and a floor surface, and that measures weight of an object placed on the table-top.

10. A table, comprising:
a table-top configured to place thereon a subject;
a plurality of measurement units that outputs a set of first measurement signals corresponding to weight of the subject placed on the table-top; and
processing circuitry configured to
acquire a first measurement mode indicating a mode for measuring the weight of the subject placed on the table-top; and
estimate the weight of the subject placed on the table-top by acquiring from a memory a weight value corresponding to the first measurement mode and the set of the respective first measurement signals of the plurality of measurement units, the memory storing second measurement modes each indicating a mode for measuring weight of a subject, sets of respective second measurement signals of the plurality of measurement units, and weight values associated with each other.

11. A control method of a medical image diagnostic apparatus that includes a table-top on which a subject is placed, and a plurality of measurement units that outputs a set of first measurement signals corresponding to weight of the subject placed on the table-top, the control method comprising:
acquiring a first measurement mode indicating a mode for measuring the weight of the subject placed on the table-top; and
estimating the weight of the subject placed on the table-top by acquiring from a memory a weight value corresponding to the first measurement mode and the set of the respective first measurement signals of the plurality of measurement units, the memory storing second measurement modes each indicating a mode for measuring weight of a subject, sets of respective second measurement signals of the plurality of measurement units, and weight values associated with each other.

* * * * *